United States Patent [19]

Floyd, Jr. et al.

[11] Patent Number: 4,474,809
[45] Date of Patent: Oct. 2, 1984

[54] ARYLGLYOXALS

[75] Inventors: Middleton B. Floyd, Jr., Suffern, N.Y.; Vern G. DeVries, Ridgewood, N.J.

[73] Assignee: American Cyanamid Company, Stamford, Conn.

[21] Appl. No.: 459,449

[22] Filed: Jan. 20, 1983

[51] Int. Cl.³ .................. A61K 31/185; A61K 31/32; C07C 143/42; C07C 49/76
[52] U.S. Cl. .................................... 424/315; 424/331; 260/511; 568/329; 568/330; 568/331
[58] Field of Search ................ 260/511; 568/337, 331, 568/329, 330; 424/315, 331

[56] References Cited

PUBLICATIONS

Chem. Abstract, vol. 87, No. 13, 102056m, p. 593, 1977.
Chem. Abstract, vol. 90, No. 17, 137490n, p. 482, 1979.
Chem. Abstract, vol. 94, No. 9, 65295k, p. 690, 1981.

*Primary Examiner*—Nicky Chan
*Attorney, Agent, or Firm*—Edward A. Conroy, Jr.

[57] ABSTRACT

Arylglyoxals which are new compounds active as hypoglycemic agents.

28 Claims, No Drawings

ARYLGLYOXALS

BACKGROUND OF THE INVENTION

This invention relates to arylglyoxals and to hydrates and sodium bisulfite adducts formed from them, which are new compounds useful as pharmaceutical agents. The novel compounds of this invention are hypoglycemic agents capable of ameliorating diabetes mellitus in mammals by acting to simulate and/or potentiate the action of insulin. This invention further relates to methods for treating diabetes mellitus in mammals in need of such treatment. In addition, this invention is concerned with pharmaceutical compositions for the utilization of these compounds in the treatment of diabetes mellitus. Further, this invention relates to the chemical synthesis of the compound disclosed herein.

The disease diabetes mellitus is characterized by metabolic defects in the production and utilization of glucose which result in the failure to maintain appropriate blood sugar levels. Research on the treatment of diabetes has centered on attempts to normalize fasting and postprandial blood glucose levels. Treatments have included parenteral administration of exogenous insulin, oral administration of drugs and dietary therapies.

Initially it was thought that hyperglycemia was simply the result of a deficiency in the supply of insulin, the principle hormone which controls glucose metabolism. As a result, research focused on the source of insulin production, the beta cells of the pancreas, and pharmaceutical agents were discovered which stimulated the production of insulin by the pancreas. Although it remains true that a deficiency of insulin does cause hyperglycemia it has now been recognized that other metabolic defects can be a major cause of elevated blood glucose.

In Type I diabetes, also called juvenile onset or insulin-dependent diabetes, insulin deficiency is indeed the cause of hyperglycemia. However, the majority of diabetics suffer from a form of the disease referred to as Type II diabetes, also called maturity onset or noninsulin dependent diabetes. The main characteristic displayed by Type II diabetics is insulin resistance or insulin insensitivity. Insulin resistance is a condition in which available insulin, secreted by the pancreas and circulating in the blood stream, fails to stimulate sufficient glucose uptake and utilization in insulin sensitive tissue. This inability of peripheral tissues including liver, muscle and fat, whose metabolic machinery is normally sensitive to insulin, to utilize glucose efficiently, results in elevated blood glucose.

Compounds which simulate and/or potentiate the biological action of insulin would be beneficial in the treatment of hyperglycemia resulting from mild to moderate insulin insufficiency or insulin insensitivity. A compound which would simulate or mimic insulin's action would correct both insulin deficiency and insulin resistance by its own insulin-like action. Further, a compound which would potentiate insulin's action would correct insulin deficiency by rendering the small amount of insulin which is present more efficacious and would correct insulin resistance directly by acting synergistically to make insulin more effective. Thus compounds which show insulin-like and/or insulin potentiating activity would be beneficial for the treatment of hyperglycemia occuring either in Type I or Type II diabetes.

The compounds of the present invention simulate and potentiate the biological action of insulin. They simulate insulin's action by promoting the cellular uptake and metabolism of glucose in the absence of insulin. They potentiate insulin's action by exerting a synergistic effect on the cellular uptake and metabolism of glucose in the presence of sub-maximal concentrations of insulin. The exact mechanism by which the compounds of this invention act to produce these effects is not known and the invention should not be construed as limited to any particular mechanism of action. None the less, the compounds of this invention are useful for the treatment of hyperglycemia and diabetes in mammals.

SUMMARY OF THE INVENTION

This invention relates to new arylglyoxals and their addition products, their use in the treatment of diabetes mellitus, pharmaceutical compositions containing them and their chemical synthesis. More particularly, it is concerned with compounds which may be represented by the formula:

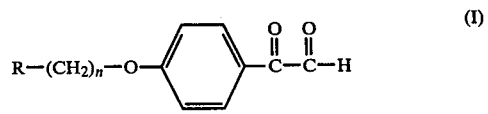

(I)

wherein n is an integer from 1 to 4; R is selected from the group consisting of (C$_4$-C$_6$) cycloalkyl, phenyl, pentafluorophenyl and monosubstituted phenyl wherein the substituent is fluoro, chloro, methyl, methoxy, trifluoromethyl or phenoxy; with the proviso that when n is 1 then R may not be phenyl; and the hydrates and sodium bisulfite adducts thereof.

This invention is further concerned with a method of treating diabetes mellitus in a mammal in need of such treatment which comprises administering to said mammal an effective amount of a compound as recited above.

This invention also relates to a method of treating hyperglycemia in a mammal in need of such treatment which comprises administering to said mammal an effective amount of a compound as recited above.

This invention also relates to a pharmaceutical composition which comprises an effective antidiabetic amount of a compound as recited above in association with a pharmaceutically acceptable carrier.

This invention also relates to a pharmaceutical composition which comprises an effective hypoglycemic amount of a compound as recited above in association with a pharmaceutically acceptable carrier.

Finally, this invention relates to processes for preparing compounds as recited above.

DETAILED DESCRIPTION OF THE INVENTION

The compounds of this invention may be prepared according to the following reaction sequence:

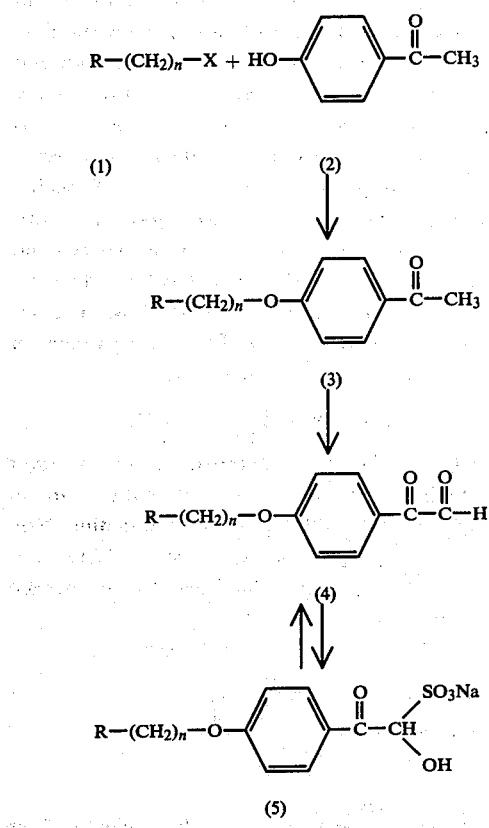

In accordance with the above reaction sequence, a compound of the formula (1) where R and n are as described hereinabove and X is chlorine or bromine, is reacted with 4-hydroxyacetophenone (2) and potassium carbonate in an organic solvent at reflux for 8–24 hours, then poured into cold water and extracted with an organic solvent giving the acetophenone (3). The acetophenone (3) is then dissolved in dimethyl sulfoxide and treated with aqueous hydrobromic acid at 45°–65° C. for 18–48 hours, poured into ice and extracted with ethyl acetate. The extract containing (4) wherein m may vary from almost zero to one or more, is concentrated, dissolved in a mixture of ethanol and water at 50°–70° C. and treated with sodium metabisulfite at the boiling point for 5 minutes, then cooled under argon at 0° C., giving (5). The sodium bisulfite derivative (5) is then suspended in water at 40°–60° C., acidified, heated at 90°–100° C., for 1–2 hours, cooled and extracted with ether. The ether extract is concentrated giving (4). Compounds of structure (4) are obtained in various degrees of hydration; that is, m may vary from almost zero to one or more.

Alternatively, the acetophenone (3), is treated with selenium dioxide in aqueous dioxane at reflux, under an inert atmosphere for 12–24 hours. The reaction mixture is then filtered and the filtrate evaporated, giving (4) which may then be converted to (5) by treatment with sodium bisulfite in aqueous ethanol as described above.

The compounds of this invention were tested for their insulin-like and insulin-potentiating activity according to the following procedure:

Male, Wistar strain, Royal Hart rats weighing 125–170 g. were sacrificed by decapitation. Their abdominal cavities were opened and distal or thin portions of epididymal fat pads excised, accumulated, and placed in 0.9% saline. The tissue was weighed and placed at a density of about 0.4 g./ml. in Krebs-Henseleit bicarbonate (KHB) buffer containing 5 mg. of crude bacterial collagenase per ml. [The KHB is composed of 118 mM sodium chloride; 4.7 mM potassium chloride; 1.2 mM calcium chloride; 1.2 mM potassium dihydrogen phosphate; 1.2 mM magnesium sulfate heptahydrate; 25 mM sodium bicarbonate and 0.3 mM glucose and is saturated with oxygen:carbon dioxide (95.5).] The tissues were incubated with collagenase for one hour at 37° C. with gentle agitation in a Dubnoff metabolic shaker. At the end of this digestion period the cells were washed five times with twice their volume of KHB buffer containing fatty acid free bovine serum albumin (Pentex Fraction V) at a concentration of 3%. The digest was filtered through two layers of gauze and suspended in KHB buffer with albumin to a volume ten times the initial total weight of the fat pads. Incubation of one ml. aliquots of the cell suspension was carried out in 17×100 mm plastic Falcon tubes. Cells were incubated in the presence or absence of test compound and insulin. All tubes contained 0.15 $\mu$Ci D-glucose-U-$^{14}$C (specific activity >200 mC/mole).

Recrystallized porcine insulin (specific activity=25.5 U/mg.) was dissolved in 0.9% saline adjusted to pH 3 with hydrochloric acid. The insulin was added to the cells at a concentration of approximately 5 $\mu$U/ml. and control or basal cells received comparable volumes of pH 3 saline. Test compounds were dissolved in 50% dimethyl sulfoxide-50% ethanol and added to the cells at a concentration of 100 $\mu$g./ml. Control cells received comparable volumes of dimethyl sulfoxide-ethanol.

After the tubes were loaded with insulin and test compound, or other vehicles, and cell suspension, they were capped with sleeve stoppers fitted with hanging, plastic center wells. Each well contained a small section of folded filter paper. The tubes were then gassed for about one minute with oxygen:carbon dioxide (95:5) via needles inserted through the septum of the stopper. Immediately after gassing, the radioactive glucose was injected into the incubate and the tubes were placed in a 37° C. metabolic shaking water bath and were incubated for one hour with agitation.

At the end of the incubation, 0.4 ml. of Hyamine hydroxide and then 0.5 ml. of 5N sulfuric acid were carefully injected into the center well and cell suspension, respectively. The acidified cell suspension was then incubated an additional 30 minutes at room temperature with gentle agitation. At the end of this carbon dioxide collection period, the center wells were dropped into vials containing 10 ml. of Dimiscint® scintillation cocktail and the radioactivity counted by liquid scintillation spectrometry.

The measurement of carbon dioxide radioactivity in counts per minute produced by these cells in the absence of both test compounds and insulin is the basal level (b). Radioactivity produced in the presence of test compounds only, insulin only and both test compound and insulin are (c), (i) and (ci), respectively. Each of (c), (i) and (ci) is then expressed as a percent of the basal value:

$$C = \frac{c}{b} \; ; \; I = \frac{i}{b} \; ; \; CI = \frac{ci}{b}.$$

Finally, insulin-like activity (%C/I) is calculated using the formula $$\%C/I = \frac{(100)(C - 100)}{(I - 100)};$$

and insulin-potentiating activity (%P) is calculated using the formula $$\%P = \frac{(100)(CI - C - I + 100)}{(I - 100)}.$$

The results of this test on representative compounds of this invention appear in Table I.

TABLE I

| Compound | % C/I | % P |
|---|---|---|
| [p-(cyclohexylmethoxy)phenyl]glyoxal hemihydrate | 229 | 170 |
| (α-cyclohexyl-p-anisoyl)hydroxy-methanesulfonic acid, sodium salt | 496 | 267 |
| α-hydroxy-β-oxo-4-(2-phenylethoxy)-benzeneethanesulfonic acid, sodium salt | 466 | 197 |
| 4-[[2-[4-(cyclohexylmethoxy)phenyl]-2-oxo-1-hydroxyethyl]amino]-benzoic acid | 284 | 0 |
| 4-[[3-(trifluoromethyl)phenyl]methoxy]-α-oxo-benzeneacetaldehyde hemihydrate | 419 | 0 |
| 4-[(3-fluorophenyl)methoxy]-α-oxo-benzeneacetaldehyde hemihydrate | 114 | 55 |
| α-hydroxy-β-oxo-4-[[3-(trifluoromethyl)phenyl]methoxy]benzeneethanesulfonic acid, sodium salt | 476 | 111 |
| α-oxo-4-[[4-(trifluoromethyl)phenyl]methoxy]-benzeneacetaldehyde hydrate | 359 | 46 |
| 4-[(3-chlorophenyl)methoxy]-α-oxo-benzeneacetaldehyde hydrate | 441 | 34 |
| 4-[2-(4-fluorophenyl)ethoxy]-α-hydroxy-β-oxo-benzeneethanesulfonic acid, sodium salt | 471 | 0 |
| 4-[(3-fluorophenyl)methoxy]-α-hydroxy-β-oxo-benzeneethanesulfonic acid, sodium salt | 370 | 0 |
| 4-[(4-fluorophenyl)methoxy]-α-oxo-benzeneacetaldehyde hemihydrate | 248 | 0 |
| 4-[(2-fluorophenyl)methoxy]-α-hydroxy-β-oxo benzeneethanesulfonic acid, sodium salt | 293 | 0 |
| α-hydroxy-β-oxo-4-[2-[3-(trifluoromethyl)-phenyl]ethoxy]-benzeneethanesulfonic acid, sodium salt | 350 | 0 |
| α-hydroxy-β-oxo-4-[[4-(trifluoromethyl)phenyl]-methoxy]-benzeneethanesulfonic acid, sodium salt | 496 | 175 |
| 4-[(3-chlorophenyl)methoxy]-α-hydroxy-β-oxo-benzeneethanesulfonic acid, sodium salt | 288 | 138 |
| α-oxo-4-[(pentafluorophenyl)methoxy]-benzeneacetaldehyde hydrate | 1076 | 259 |
| 4-[(4-chlorophenyl)methoxy]-α-oxo-benzeneacetaldehyde hydrate | 692 | 33 |
| α-oxo-4-[(3-phenoxyphenyl)methoxy]-benzeneacetaldehyde hemihydrate | 277 | 152 |
| 4-[(4-fluorophenyl)methoxy]-α-hydroxy-β-oxo-benzeneethanesulfonic acid, sodium salt | 406 | 277 |
| 4-(cyclobutylmethoxy)-α-hydroxy-β-oxo-benzeneethanesulfonic acid, sodium salt | 296 | 274 |
| 4-[(4-methoxyphenyl)methoxy]-α-oxo-benzeneacetaldehyde | 270 | 83 |
| 4-[(4-chlorophenyl)methoxy]-α-hydroxy-β-oxo-benzeneethanesulfonic acid, sodium salt | 638 | 355 |
| α-hydroxy-β-oxo-4-[(pentafluorophenyl)methoxy]-benzeneethanesulfonic acid, sodium salt | 668 | 188 |
| α-hydroxy-β-oxo-[(3-phenoxyphenyl)methoxy]-benzeneethanesulfonic acid, sodium salt | 83 | 139 |
| α-hydroxy-β-oxo-4-[(4-methylphenyl)methoxy]-benzeneethanesulfonic acid, sodium salt | 73 | 77 |
| α-hydroxy-4-[(4-methoxyphenyl)methoxy]-β-oxo-benzeneethanesulfonic acid, sodium salt | 297 | 146 |
| 4-[(4-methylphenyl)methoxy]-α-oxo-benzeneacetaldehyde hydrate | 591 | 148 |

When the compounds are employed for the above utility, they may be combined with one or more pharmaceutically acceptable carriers, e.g., solvents, diluents and the like, and may be administered orally in such forms as tablets, capsules, dispersible powders, granules, or suspenisons containing, for example, from about 0.5 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.5 to 5% suspending agent in an isotonic medium. These pharmaceutical preparations may contain, for example, from about 0.5% up to about 90% of the active ingredient in combination with the carrier, more usually between 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 5 milligrams to about 100 milligrams per kilogram of animal body weight, preferably given in divided doses two to four times a day, or in sustained release form. For most large mammals, the total daily dosage is from about 500 milligrams to about 5,000 milligrams preferably from about 350 milligrams to 3,500 milligrams. Dosage forms suitable for internal use comprise from about 25 to 500 milligrams of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered orally as well as by intravenous, intramuscular, or subcutaneous routes if necessary. Solid carriers include starch, lactose, dicalcium phosphate, microcrystalline celulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, e.g., vitamin E, ascorbic acid, BHT and BHA.

The preferred pharmaceutical compositions from the stand-point of ease of preparation and administration are solid composition, particularly tablets and hard-filled or liquid-filled capsules. Oral adminsitration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The invention will be more fully described in conjunction with the following specific examples which are not to be construed as limiting the scope of the invention.

EXAMPLE 1

4'-(Phenethyloxy)acetophenone

A stirred mixture of 18.5 g. of phenethylbromide, 20.4 g. of p-hydroxyacetophenone, 17.3 g. of anhydrous potassium carbonate and 150 ml. of acetone was refluxed under argon for 22 hours. The reaction was then cooled and partitioned between ether and water. The ether layer was washed with water and then extracted with two 100 ml. portions of cold 1N sodium hydroxide. These extracts were combined, washed with water and brine, dried and evaporated to an oil. The oil was purified by chromatography, giving the desired intermediate as a light yellow oil.

Reaction of other substituted alkyl halides of formula (1) as hereinabove described with p-hydroxyacetophenone according to the procedure of Example 1 gave the acetophenone intermediates of Examples 2–16, listed in Table II.

TABLE II

| Example | Intermediate | Physical Constant |
|---|---|---|
| 2 | 4'-(cyclohexylmethoxy)acetophenone | mp 42–43° C. |
| 3 | 1-[4-[[3-(trifluoromethyl)phenyl]methoxy]phenyl]ethanone | mp 86–87.5° C. |
| 4 | 1-[4-[(3-fluorophenyl)methoxy]phenyl]ethanone | mp 82–84° C. |
| 5 | 1-[4-[[4-(trifluoromethyl)phenyl]methoxy]phenyl]ethanone | mp 75–77° C. |
| 6 | 1-[4-[(3-chlorophenyl)methoxy]phenyl]ethanone | mp 75–77° C. |
| 7 | 1-[4-2-(4-fluorophenyl)ethoxy]phenyl]ethanone | mp 50–52° C. |
| 8 | 1-[4-[(4-fluorophenyl)methoxy]phenyl]ethanone | mp 71–73° C. |
| 9 | 1-[4-[2-[3-(trifluoromethyl)phenyl]ethoxy]phenyl]ethanone | yellow oil |
| 10 | 1-[4-[(pentafluorophenyl)methoxy]phenyl]ethanone | mp 87–90° C. |
| 11 | 1-[4-[(4-chlorophenyl)methoxy]phenyl]ethanone | mp 89–91° C. |
| 12 | 1-[4-[(3-phenoxyphenyl)methoxy]phenyl]ethanone | mp 54–57° C. |
| 13 | 1-[4-(cyclobutylmethoxy)phenyl]ethanone | bp 100–110° C. (0.1 mm Hg) |
| 14 | 1-[4-[(4-methoxyphenyl)methoxy]phenyl]ethanone | mp 127–129° C. |
| 15 | 1-[4-[(4-methylphenyl)methoxy]phenyl]ethanone | mp 102–104° C. |
| 16 | 1-[4-[(2-fluorophenyl)methoxy]phenyl]ethanone | mp 88–89° C. |

EXAMPLE 17

α-Hydroxy-β-oxo-b 4-(2-phenylethoxy)-benzeneethanesulfonic acid, sodium salt To a solution of 6.3 g. of 4'-(phenethyloxy)-acetophenone in 44 ml. of dimethyl sulfoxide was slowly added 8.84 ml. of 48% aqueous hydrobromic acid. The mixture was stirred at 55° C. for 16 hours, then poured into ice water and extracted with ethyl acetate. The extract was washed with water, then aqueous sodium bicarbonate and finally brine, dried and evaporated, giving 7.0 g. of an amber oil which is the glyoxal hydrate corresponding to the title compound.

This oil was dissolved in 90 ml. of warm ethanol, stirred, and treated with a solution of 2.85 g. of sodium bisulfite in 45 ml. of water. This mixture was refluxed for 15 minutes, filtered while hot, concentrated to ⅔ of its original volume and then cooled to 0° C. The solid was collected, washed with cold ethanol:water (3:1), ethanol, ether, and dried, giving the desired product as a white solid, m.p. 165°–180° C. (dec.).

Following the procedure of Example 17 but using the acetophenones of Examples 1–16, the products of Examples 18–39 were obtained as indicated in Table III.

TABLE III

| Example | Intermediate of Example | Product | Physical Constant |
|---|---|---|---|
| 18 | 3 | 4-[[3-(trifluoromethyl)phenyl]methoxy]-α-oxo-benzeneacetaldehyde hemihydrate | mp 86–95° C. |
| 19 | 4 | 4-[(3-fluorophenyl)methoxy]-α-oxo-benzeneacetaldehyde hemihydrate | mp 114–116° C. |
| 20 | 3 | α-hydroxy-β-oxo-4-[[3-(trifluoromethyl)phenyl]methoxy]-benzeneethanesulfonic acid, sodium salt | mp 203° C. |
| 21 | 5 | α-oxo-4-[[4-(trifluoromethyl)phenyl]methoxy]-benzeneacetaldehyde hydrate | mp 115–120° C. |
| 22 | 6 | 4-[(3-chlorophenyl)methoxy]-α-oxo-benzeneacetaldehyde hemihydrate | mp 107–112° C. |
| 23 | 7 | 4-[2-(4-fluorophenyl)-ethoxy]-α-hydroxy-β-oxo-benzeneethanesulfonic acid, sodium salt | mp 160–185° C. (dec.) |
| 24 | 4 | 4-[(3-fluorophenyl)methoxy]-α-hydroxy-β-oxo-benzeneethanesulfonic acid sodium salt | mp 345–350° C. |
| 25 | 8 | 4-[(4-fluorophenyl)methoxy]-α-oxo-benzeneacetaldehyde hemihydrate | mp 107–113° C. |
| 26 | 16 | 4-[(2-fluorophenyl)methoxy]-α-hydroxy-β-oxo-benzeneethanesulfonic acid, sodium salt | mp 197° C. |
| 27 | 9 | α-hydroxy-β-oxo-4-[2-[3-(trifluoromethyl)phenyl]ethoxy]-benzeneethanesulfonic acid, sodium salt | mp 140–160° C. (dec.) |
| 28 | 5 | α-hydroxy-β-oxo-4-[[4-(trifluoromethyl)phenyl]methoxy]-benzeneethanesulfonic | mp 180° C. |

TABLE III-continued

| Example | Intermediate of Example | Product | Physical Constant |
|---|---|---|---|
| 29 | 6 | 4-[(3-chlorophenyl)methoxy]-α-hydroxy-β-oxo-benzeneethanesulfonic acid, sodium salt | mp 190° C. |
| 30 | 10 | α-oxo-4-[(pentafluorophenyl)methoxy]-benzeneacetaldehyde hydrate | mp 82-104° C. (dec.) |
| 31 | 11 | 4-[(4-chlorophenyl)methoxy]-α-oxo-benzeneacetaldehyde hydrate | mp 115-124° C. |
| 32 | 2 | α-cyclohexyl-p-anisoyl)hydroxy-methanesulfonic acid, sodium salt | mp 180° C. |
| 33 | 12 | α-oxo-4-[(3-phenoxyphenyl)methoxy]-benezeneacetaldehyde hemihydrate | mp 47-58° C. |
| 34 | 8 | 4-[(4-fluorophenyl)methoxy]-α-hydroxy-β-oxo-benzeneethanesulfonic acid, sodium salt | mp 320° C. (dec.) |
| 35 | 13 | 4-(cyclobutylmethoxy)-α-hydroxy-β-oxo-benzeneethanesulfonic acid, sodium salt | mp 180° C. |
| 36 | 11 | 4-[(4-chlorophenyl)methoxy]-α-hydroxy-β-oxo-benzeneethanesulfonic acid, sodium salt | mp 205° C. |
| 37 | 10 | α-hydroxy-β-oxo-4-[(pentafluorophenyl)-methoxy]-benzeneethanesulfonic acid, sodium salt | mp 250° C. |
| 38 | 12 | α-hydroxy-β-oxo-[(3-phenoxyphenyl)-methoxy]-benzeneethanesulfonic acid, sodium salt | mp 190° C. |
| 39 | 15 | α-hydroxy-β-oxo-4-[(4-methylphenyl)-methoxy]-benzeneethanesulfonic acid, sodium salt | mp 220° C. |

EXAMPLE 40

[p-(Cyclohexylmethoxy)phenyl]glyoxal hemihydrate

A mixture of 12.0 g of 4'-(cyclohexylmethoxy)acetophenone, 5.8 g of selenium dioxide, 1.4 ml of water and 70 ml of p-dioxane was refluxed with stirring at 120° C. for 18.5 hours, cooled and filtered through diatomaceous earth, washing with p-dioxane. The combined filtrate and wash was poured into 200 ml of water cooled to 8° C. The yellow solid was collected and dried. An 8.1 g portion of sodium bisulfite was dissolved in 500 ml of water. To this was added a solution of the above solid in a mixture of 300 ml of ethanol and 100 ml of p-dioxane. The resulting mixture was filtered and the filtrate stored at 0° C. for 48 hours. The resulting solid was collected, washed twice with water, p-dioxane and absolute ethanol and then dried. This solid was added to 535 ml of 0.5N hydrochloric acid and heated with stirring at 75° C. for 8 minutes and then cooled to 10° C. The solid was collected, dissolved in hot p-dioxane, filtered and 20 ml of water added to the filtrate. The filtrate was cooled to 0° C., giving the desired product as a white solid, m.p. 118°-121° C.

EXAMPLE 41

4-[(4-Methoxyphenyl)methoxy]-α-oxo-benzeneacetaldehyde hydrate

A 10.0 g portion of 1-[4-[(4-methoxyphenyl)-methoxy]phenyl]ethanone was dissolved in 50 ml of hot p-dioxane. A 2.0 ml portion of water and 4.4 g of selenium dioxide were added and the mixture was stirred at reflux for 67 hours, then cooled and filtered through diatomaceous earth. The filtrate was poured into 300 ml of water and the solid collected. This solid was extracted with eight 100 ml portions of ethyl acetate. The extracts were combined, washed with water, dried and evaporated. The residue was dissolved in 100 ml of boiling toluene, treated with charcoal and filtered through diatomaceous earth. The filtrate was treated with 200 ml. of hexane, giving the desired product as a pale yellow solid, m.p. 127°-138° C.

EXAMPLE 42

α-Hydroxy-4-[(4-methoxyphenyl)methoxy]-β-oxo-benzeneethanesulfonic acid, sodium salt A 2.8 g. portion of 4-[(4-methoxyphenyl)-methoxy]-α-oxo-benzeneacetaldehyde hydrate was dissolved in 100 ml. of absolute ethanol and 100 ml. of methyl cellosolve with boiling. A solution of 1.25 g. of sodium bisulfite in 7 ml. of water was added and the mixture was heated on a steam bath for 15 minutes, then allowed to stand overnight. The solid was collected and washed with methyl cellosolve, water and then absolute ethanol, then dried, giving the desired product as a white solid, m.p. 200°-205° C.

EXAMPLE 43

4-[(4-Methylphenyl)methoxy]-α-oxo-benzeneacetaldehyde hydrate

A 2.8 g. portion of α-hydroxy-β-oxo-4-[(4-methylphenyl)methoxy]-benzeneethanesulfonic acid, sodium salt was combined with 25 ml. of 0.5N hydrochloric acid, heated on a steam bath for 5 minutes and then allowed to stand for several hours. The solid was collected, slurried with 50 ml. of acetone, 25 ml. of 0.5N hydrochloric acid were added and the mixture was refluxed for 2 hours. The solid was collected, again refluxed with acid and the solid collected, washed free of acid and dried, giving the desired product as a white solid, m.p. 125°-130° C.

EXAMPLE 44

4-[[2-[4-(Cyclohexylmethoxy)phenyl]-2-oxo-1-hydroxyethyl]amino]-benzoic acid

A mixture of 2.3 g. of [p-(cyclohexylmethoxy)-phenyl]glyoxal hemihydrate, 1.06 g. of p-aminobenzoic acid, 50 ml. of tetrahydrofuran and 17 ml. of water was heated at boiling for 45 minutes, stripped of tetrahydrofuran and the solid collected. This solid was recrystallized from 200 ml. of acetonitrile, then dissolved in boiling acetone, filtered while hot and 200 ml. of water added to the hot filtrate. This mixture was cooled to 0° C. and the solid collected, giving the desired product as a pale yellow solid, m.p. 188°–190° C.

We claim:

1. A compound selected from the group consisting of those of the formula:

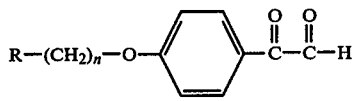

wherein n is an integer from 1 to 4; R is ($C_4$–$C_6$) cycloalkyl, pentafluorophenyl or monosubstituted phenyl wherein the substitutent is fluoro, chloro, methoxy, phenoxy or trifluoromethyl; the hydrates thereof; and the sodium bisulfite adducts thereof.

2. The compound according to claim 1, [p-(cyclohexylmethoxy)phenyl]glyoxal hemihydrate.

3. The compound according to claim 1, (α-cyclohexyl-p-anisoyl)hydroxy-methanesulfonic acid, sodium salt.

4. The compound according to claim 1, α-hydroxy-β-oxo-4-[(pentafluorophenyl)methoxy]benzeneethanesulfonic acid, sodium salt.

5. The compound according to claim 1, α-hydroxy-β-oxo-[(3-phenoxyphenyl)methoxy]-benzeneethanesulfonic acid, sodium salt.

6. The compound according to claim 1, α-hydroxy-4-[(4-methoxyphenyl)methoxy]-β-oxo-benzeneethanesulfonic acid, sodium salt.

7. The compound according to claim 1, 4-[(3-fluorophenyl)methoxy]-α-oxo-benzeneacetaldehyde, hemihydrate.

8. The compound according to claim 1, α-hydroxy-β-oxo-4-[[3-(trifluoromethyl)phenyl]methoxy]-benzeneethanesulfonic acid, sodium salt.

9. The compound according to claim 1, α-oxo-4-[[4-(trifluoromethyl)phenyl]methoxy]benzeneacetaldehyde hydrate.

10. The compound according to claim 1, 4-[(3-chlorophenyl)methoxy]-α-oxo-benzeneacetaldehyde hemihydrate.

11. The compound according to claim 1, 4-[2-(4-fluorophenyl)ethoxy]-α-hydroxy-β-oxo-benzeneethanesulfonic acid, sodium salt.

12. The compound according to claim 1, 4-[(3-fluorophenyl)methoxy]-α-hydroxy-β-oxo-benzeneethanesulfonic acid, sodium salt.

13. The compound according to claim 1, 4-[(4-fluorophenyl)methoxy]-α-oxo-benzeneacetaldehyde hemihydrate.

14. The compound according to claim 1, 4-[(2-fluorophenyl)methoxy]-α-hydroxy-β-oxo-benzeneethanesulfonic acid, sodium salt.

15. The compound according to claim 1, α-hydroxy-β-oxo-4-[2-[3-(trifluoromethyl)phenyl]ethoxy]benzeneethanesulfonic acid, sodium salt.

16. The compound according to claim 1, α-hydroxy-β-oxo-4-[[4-(trifluoromethyl)phenyl]methoxy]benzeneethanesulfonic acid, sodium salt.

17. The compound according to claim 1, 4-[(3-chlorophenyl)methoxy]-α-hydroxy-β-oxo-benzeneethanesulfonic acid, sodium salt.

18. The compound according to claim 1, α-oxo-4-[(pentafluorophenyl)methoxy]benzeneacetaldehyde hydrate.

19. The compound according to claim 1, 4-[(4-chlorophenyl)methoxy]-α-oxo-benzeneacetaldehyde hydrate.

20. The compound according to claim 1, α-oxo-4-[(3-phenoxyphenyl)methoxy]-benzeneacetaldehyde hemihydrate.

21. The compound according to claim 1, 4-[(4-fluorophenyl)methoxy]-α-hydroxy-β-oxo-benzeneethanesulfonic acid, sodium salt.

22. The compound according to claim 1, 4-(cyclobutylmethoxy)-α-hydroxy-β-oxo-benzeneethanesulfonic acid, sodium salt.

23. The compound according to claim 1, 4-[(4-methoxyphenyl)methoxy]-α-oxo-benzeneacetaldehyde hemihydrate.

24. The compound according to claim 1, 4-[(4-chlorophenyl)methoxy]-α-hydroxy-β-oxo-benzeneethanesulfonic acid, sodium salt.

25. A method of treating diabetes mellitus in a mammal in need of such treatment which comprises administering to said mammal an effective amount of a compound selected from those of claim 1.

26. A method of treating hyperglycemia in a mammal in need of such treatment which comprises administering to said mammal an effective amount of a compound selected from those of claim 1.

27. A pharmaceutical antidiabetic composition which comprises an effective antidiabetic amount of a compound as recited in claim 1 or 2 in association with a pharmaceutically acceptable carrier.

28. A pharmaceutical hypoglycemic composition which comprises an effective hypoglycemic amount of a compound as recited in claim 1 or 2 in association with a pharmaceutically acceptable carrier.

* * * * *